(12) United States Patent
Tran et al.

(10) Patent No.: US 8,090,824 B2
(45) Date of Patent: Jan. 3, 2012

(54) GATEWAY DATA PROXY FOR EMBEDDED HEALTH MANAGEMENT SYSTEMS

(75) Inventors: My Tran, Albuquerque, NM (US); Al Salinas, Albuquerque, NM (US)

(73) Assignee: Honeywell International, Inc., Morristown, NJ (US)

( * ) Notice: Subject to any disclaimer, the term of this patent is extended or adjusted under 35 U.S.C. 154(b) by 0 days.

(21) Appl. No.: 12/645,921

(22) Filed: Dec. 23, 2009

(65) Prior Publication Data

US 2011/0154118 A1 Jun. 23, 2011

(51) Int. Cl.
G06F 13/00 (2006.01)
(52) U.S. Cl. .................. 709/224; 709/202; 709/219
(58) Field of Classification Search .................. 709/201, 709/202, 203, 217, 219, 223, 224
See application file for complete search history.

(56) References Cited

U.S. PATENT DOCUMENTS

| | | | |
|---|---|---|---|
| 6,199,018 B1 | 3/2001 | Quist et al. | |
| 6,236,909 B1 | 5/2001 | Colson et al. | |
| 6,370,449 B1 | 4/2002 | Razavi et al. | |
| 6,446,123 B1 * | 9/2002 | Ballantine et al. | 709/224 |
| 6,738,811 B1 * | 5/2004 | Liang | 709/224 |
| 6,928,345 B2 | 8/2005 | Quinn | |
| 7,249,170 B2 * | 7/2007 | Tindal et al. | 709/223 |
| 7,302,612 B2 * | 11/2007 | Nye et al. | 714/38 |
| 7,337,183 B2 | 2/2008 | Near | |
| 2004/0176887 A1 | 9/2004 | Kent et al. | |
| 2006/0047403 A1 | 3/2006 | Volponi et al. | |
| 2006/0077917 A1 | 4/2006 | Brahmajosyula et al. | |
| 2008/0040152 A1 | 2/2008 | Vian et al. | |
| 2008/0270066 A1 | 10/2008 | Blaser et al. | |
| 2008/0312783 A1 | 12/2008 | Mansouri et al. | |
| 2009/0240472 A1 | 9/2009 | Winnebeck et al. | |

* cited by examiner

*Primary Examiner* — Viet Vu
(74) *Attorney, Agent, or Firm* — Ingrassia Fisher & Lorenz, P.C.

(57) ABSTRACT

A gateway data proxy is a system which provides the capabilities to provide and obtain the customized data across multiple platforms to facilitate the remote operations of embedded health management systems (EHMS). The system allows the collaborative works taken place among the EHMS from diagnostics, prognostics, maintenance, to maintenance history tracking. Depending on deployment needs, the system can operate as stand-alone systems or as an integrated module of the EHMS. As part of operation, the system provides logical network connection and be the broker of data between EHMS instances and between EHMS with onboard systems and other service applications.

18 Claims, 10 Drawing Sheets

GATEWAY DATA PROXY FOR EMBEDDED HEALTH MANAGEMENT SYSTEMS

STATEMENT REGARDING FEDERALLY SPONSORED RESEARCH OR DEVELOPMENT

This invention was made with Government support under Contract No. W56HZV-05-C-0724 awarded by the U.S. Army. The Government has certain rights in this invention.

FIELD OF THE INVENTION

The present invention relates generally to health management systems, and, more particularly, to systems and methods for facilitating remote diagnostic, prognostic, and maintenance, and assessing the health status at multi-levels of a plurality of platforms.

BACKGROUND OF THE INVENTION

Health management systems are utilized today on a number of platforms, such as in vehicles, airplanes, ships, and industrial controls. The health management systems typically gather data pertaining to operation of the platform in terms of sensor, equipment, sub-system, and system, and provide determinations of the current and future health of the platform based on the data. However, in some instances, to support the remote diagnostic and prognostic reasoning and performing maintenance, such health management systems may need to obtain and utilize all information that may be relevant for the determinations of health and maintenance situations from remote platforms.

Accordingly, it is desirable to provide improved systems with versatile remote capabilities for monitoring, routing, and distributing health data and assessment results in various platforms, such as vehicles, for example by incorporating persistence of equipment health information, operational data such as system and platform mode, environmental data such as terrain, weather condition, and/or other data from multiple platforms. It is also desirable to provide improved methods for monitoring health in various platforms, such as vehicles, for example by funneling health information along with operational and environment data to a remote platform for evaluations and assessment to accommodate deployment needs. Furthermore, the desirable features and characteristics of the present invention will be apparent from the subsequent detailed description and the appended claims, taken in conjunction with the accompanying drawings and the foregoing technical field and background.

BRIEF SUMMARY

In accordance with an exemplary embodiment, a system is provided. The system comprises a first processor and a second processor. The first processor is embedded within a first health management system residing on a first platform of a plurality of platforms. The first processor is configured to obtain first data pertaining to operation of the first platform from the first health management system and to provide the first data on a communication network. The second processor is embedded within a second health management system residing on a second platform of the plurality of platforms, and is coupled to the first processor. The second processor is configured to obtain second data pertaining to operation of the second platform from the second health management system, obtain the first data along the communication network, and process the first data and the second data, to thereby generate a health determination for the first platform, the second platform, or both.

In accordance with another exemplary embodiment, a method is provided for health monitoring of one or more of a plurality of platforms. The method comprises the steps of obtaining first data pertaining to operation of a first platform of the plurality of platforms from a first health management system residing on the first platform via a first processor, obtaining second data pertaining to operation of a second platform of the plurality of platforms from the second health management system via a second processor, obtaining the first data along the communication network via the second processor, and processing the first data and the second data, to thereby generate a health determination for the first platform, the second platform, or both, via the second processor.

In accordance with a further exemplary embodiment, a system is provided. The system comprises a communication network, a first processor, a second processor, and a third processor. The first processor is embedded within a first health management system residing on a first platform of a plurality of platforms. The first processor is configured to obtain first data pertaining to operation of the first platform from the first health management system and provide the first data on the communication network. The second processor is embedded within a second health management system residing on a second platform of the plurality of platforms, and is coupled to the first processor. The second processor is configured to obtain second data pertaining to operation of the second platform and provide the second data on the communication network. The third processor resides on a third platform of the plurality of platforms. The third processor is coupled to the first processor and to the second processor. The third processor is configured to obtain the first data along the communication network, obtain the second data along the communication network, and process the first data and the second data, to thereby generate a health determination for the first platform, the second platform, or both.

BRIEF DESCRIPTION OF THE DRAWINGS

The present invention will hereinafter be described in conjunction with the following drawing figures, wherein like numerals denote like elements, and.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
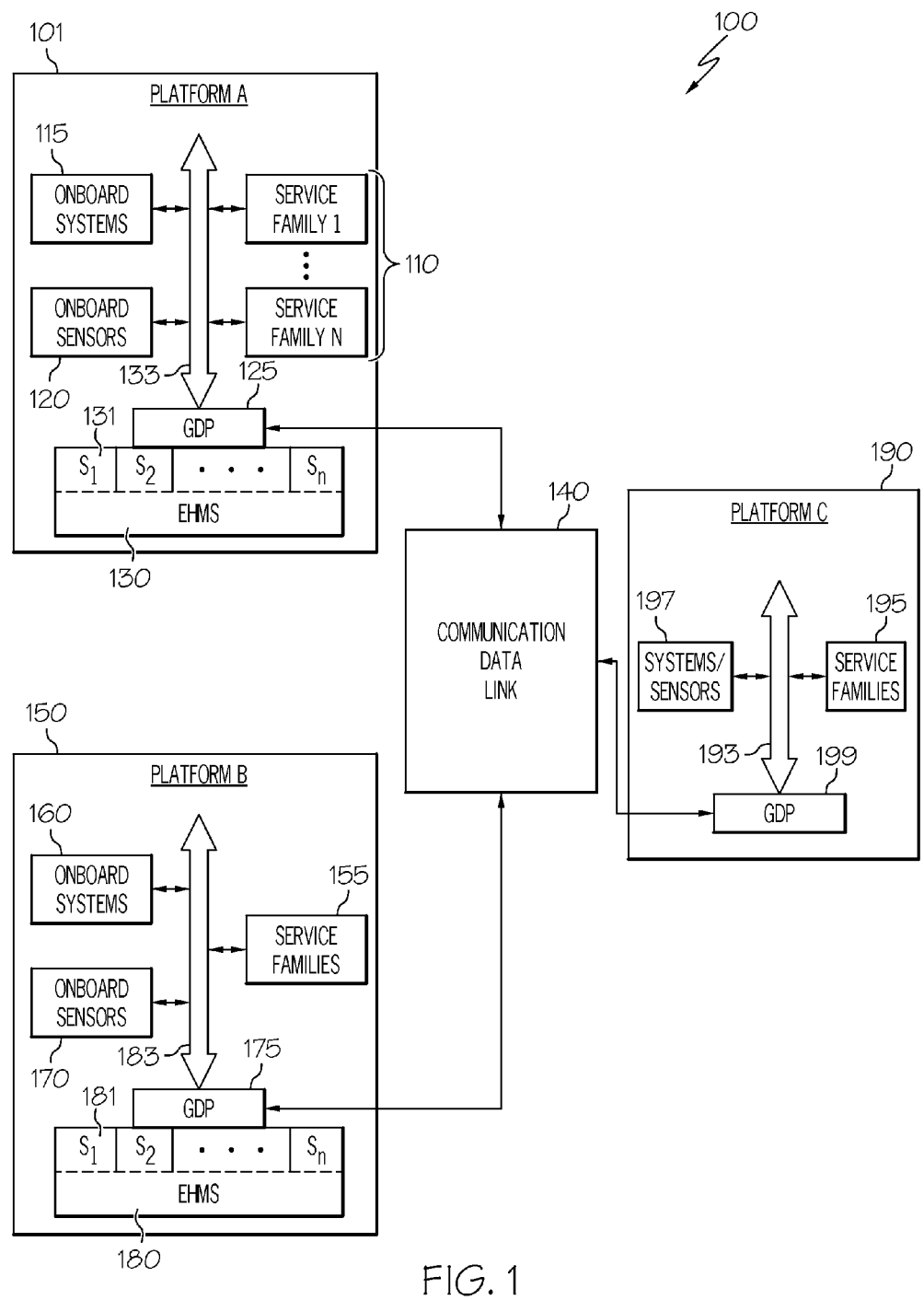
FIG. 1 is a functional block diagram of a system for monitoring health of various platforms, the system having a gateway data proxy for each of the platforms, in accordance with an exemplary embodiment.

FIG. 1 is a functional block diagram of a system 100 for monitoring health of various platforms, in accordance with an exemplary embodiment. The system 100 of FIG. 1, along with the other systems, devices, methods, and components depicted in FIGS. 1-9 and described herein, allow health management systems and methods to be scalable from a small component to a full-up system to fit with the resource constraints imposed by a host platform, and more important, to be able to leverage the computation resource availability as well as health management capabilities from other platforms.

In the depicted embodiment, three platforms are depicted, namely, Platform A (101), Platform B (150), and Platform C (190). It will be appreciated that the number of platforms in the system 100 may vary in different embodiments. Also in the depicted embodiment, the various platforms are coupled to one another via a communications data link 140.

The types of platforms may also vary in different embodiments. For example, in one exemplary embodiment, each platform comprises a land vehicle. In another exemplary embodiment, each platform comprises an airplane. In another exemplary embodiment, each platform comprises a marine vehicle. In another exemplary embodiment, Platform A (101) and Platform (B) 150 comprise land vehicles, and Platform C (190) comprises an airplane, such as an unmanned aircraft. In another exemplary embodiment, Platform A (101), Platform B (150), and Platform C (190) comprise three industrial control centers.

In another exemplary embodiment, Platform A (101) and Platform B (150) comprise land vehicles, and Platform C (190) comprises a command and control center, computer, and/or system, for example for a military operation on a battlefield. In another exemplary embodiment, Platform A (101) and Platform B (150) comprise airplanes, and Platform C (190) comprises a command and control center, computer, and/or system, such as an aircraft control center. In another exemplary embodiment, Platform A (101) and Platform B (150) comprise marine vehicles, and Platform C (190) comprises a command and control center, computer, and/or system, such as a fleet control center and/or a naval battlefield control center. In various other embodiments, any number of platforms may be utilized in the system 100, representing any number of the same or different types of vehicles, computers, control centers, and/or other types of apparatus and/or systems.

In the depicted embodiment, Platform A (101) comprises various service families 110, onboard systems 115, and onboard sensors 120, as well as an embedded health management system 130, a gateway data proxy (GDP) 125, and a connection 133. For example, in one such embodiment, Platform A (101) includes various service families 110, onboard systems 115, and onboard sensors 120, as well as an embedded health management system 130, a gateway data proxy (GDP) 125, and a connection 133 each embedded on a particular vehicle and/or other type of device and/or system.

Platform A (101) may have any number of different service families 110 (also referred to herein as local services for Platform A (101)), which are services systems that request or utilize data or information pertaining to the operation and/or health of Platform A (101) and/or components thereof. The service families 110 may include, by way of example only, some or all of the following: platform control services, environmental monitoring services, engine monitoring services, fuel monitoring services, situation awareness services, network management services, communications services, and/or any number of other different types of services for Platform A (101).

Platform A (101) may also have any number of different onboard systems 115. The onboard systems 115 preferably each include one or more systems, computers, and/or devices that interact and utilize information of the service families 110 pertaining to the operation and/or health of Platform A (101) and/or components thereof. For example, the onboard systems 115 may include, by way of example only, some or all of the following: vehicle management system, flight control system, environmental monitoring system, engine monitoring system, fuel monitoring system, display system, loading system, maintenance systems, emission control system, navigation system, vibration monitoring system, communications system, and/or any number of other different types of systems for Platform A (101).

Platform A (101) may also have any number of different onboard sensors 120. The onboard sensors 120 preferably each include one or more sensors and/or devices that measure information and/or data that are utilized by or for the service families 110 and/or the onboard systems 115 for Platform A (101). For example, the onboard sensors 120 may include, by way of example only, some or all of the following: surface control sensor, engine temperature monitoring sensor, fuel rate monitoring sensor, chemical detection sensor, motion sensor, emission control sensor, radar detection sensors, vibration monitoring sensors, fluid level sensors, and/or any number of other different types of sensors for Platform A (101).

The embedded health management system 130 provides health management, monitoring equipment health indicating data, tracking equipment and platform service history, maintenance, tracking equipment usage, diagnostics, and prognostics for Platform A (101). In certain embodiments, Platform A (101) may have multiple embedded health management systems 130. In a preferred embodiment, the embedded health management system 130 comprises a computer system having a processor, a memory, and an interface. In addition, as depicted in FIG. 1, the embedded health management system 130 also preferably includes various services 131 (also referred to herein as sibling services to the gateway data proxy (GDP) 125 that are the constructed modules of the embedded health management system (EHMS) 130 of Platform A (101).

The services 131 preferably correspond to health and maintenance reasoning and/or readiness processing of data and information pertaining to or used by the service families 110 of Platform A (101). For example, in one exemplary embodiment, services 131 of the embedded health management system 130 of Platform A (101) may include some or all of the following: diagnostics reasoning and/or processing services, prognostics reasoning and/or processing services, maintenance reasoning and/or processing services, data recording and/or processing services, consumption reasoning and/or processing services, user interaction monitoring and/or processing services, health information monitoring and/or processing services, and/or any number of other different types of services for Platform A (101).

The GDP 125 is embedded within or coupled to the embedded health management system 130. The GDP 125 facilitates the functions of the embedded health management system 130 of Platform A (101). For example, in one preferred embodiment, the GDP 125 collects data, information, and requests for the embedded health management system 130 from the service families 110, the onboard systems 115, and the onboard sensors 120 of Platform A (101) (preferably via the connection 133, described below), in addition to data, information, and requests from similar components of other remote platforms, such as Platform B (150) and Platform C (190) of FIG. 1 (preferably via the communication data link 140, described further below), among other possible platforms within the network range. The GDP 125 then distributes the collected data to local services and/or routes it to a remote GDP 175 or 199.

In addition, also in a preferred embodiment, the GDP 125 also facilitates the functions of the embedded health management systems of other platforms, such as the embedded health management system 180 of Platform B (150). For example, in one preferred embodiment, the GDP 125 collects and provides health and consumption data, platform related information, platform configuration, maintenance record, repair record, equipment usage record, platform history data, computation of availability and readiness results, interaction commands, and requests for and to the embedded health management system 180 of Platform B (150) from the service families 110, the onboard systems 115, the onboard sensors 120, and the embedded health management system 130 of Platform A (101) (preferably via the communication data link 140).

The connection 133 couples the service families 110, the onboard systems 115, the onboard sensors 120, the GDP 125, and the embedded health management system 130 of Platform A (101) of FIG. 1 to one another to facilitate the bi-directional data transfer among them. In one exemplary embodiment, the connection 133 comprises a communications bus or a network communication protocol. In another exemplary embodiment, the connection 133 comprises a wireless network. In yet other exemplary embodiments, the connection 133 may comprise any one or more of a number of different types of connections such as client and server, point to point communication, and other methods of communication.

Also in the depicted embodiment, similar to Platform A (101), Platform B (150) comprises various service families 155, onboard systems 160, and onboard sensors 170, as well as an embedded health management system 180, a gateway data proxy (GDP) 175, and a connection 183. For example, in one exemplary embodiment, Platform B (150) includes various service families 155, onboard systems 160, and onboard sensors 170, as well as an embedded health management system 180, a gateway data proxy (GDP) 175, and a connection 183, each embedded on a particular vehicle and/or other type of device and/or system.

The service families 155 (also referred to herein as local services to the GDP 175 for Platform B (150)) are service systems that request or utilize data or information pertaining to the operation and/or health of Platform B (150) and/or components thereof. Platform B (150) may have any number of different service families 155. The service families 155 may include, by way of example only, some or all of the following: situation awareness services, sensor management services, network management services, planning management services, vehicle control management services, data link management services, control and display services, and/or any number of other different types of service for Platform B (150).

Platform B (150) may also have any number of different onboard systems 160. The onboard systems 160 preferably each include one or more systems, computers, and/or devices that utilize information of the service families 155 for Platform B (150). For example, the onboard systems 160 may include, by way of example only, some or all of the following: flight control systems, environmental monitoring systems, engine monitoring systems, fuel monitoring systems, emission control systems, navigation systems, vibration monitoring systems, communications systems, and/or any number of other different types of systems for Platform B (150).

Platform B (150) may also have any number of different onboard sensors 170. The onboard sensors 170 preferably each include one or more sensors and/or devices that measure information and/or data that are utilized by or for the service families 155 and/or the onboard systems 160 for Platform B (150). For example, the onboard sensors 170 may include, by way of example only, some or all of the following: flight control sensors, environmental monitoring sensors, engine monitoring sensors, fuel monitoring sensors, emission control sensors, thermal imaging sensors, motion detection sensors, vibration monitoring sensors, chemical sensors, and/or any number of other different types of sensors for Platform B (150).

The embedded health management system 180 provides indicative health assessment capabilities for Platform B (150). In certain embodiments, Platform B (150) may have multiple embedded health management systems 180. In a preferred embodiment, the embedded health management system 180 comprises a computer system having a processor, a memory, and an interface. In addition, as depicted in FIG. 1, the embedded health management system 180 also preferably includes various services 181 (also referred to herein as sibling services to the GDP 175 for the EHMS 180 of Platform B (150)) that are the constructed modules of the embedded health management system 180.

The services 181 preferably correspond to health and maintenance reasoning and/or processing of data and information pertaining to or used by the service families 155 of Platform B (150). For example, in one exemplary embodiment, services 181 of the embedded health management system 180 of Platform B (150) may include some or all of the indicative services 131 in Platform A (101).

The GDP 175 is embedded within or coupled to the embedded health management system 180. The GDP 175 facilitates the functions of the embedded health management system 180. For example, in one preferred embodiment, the GDP 175 collects data, information, and requests for the embedded health management system 180 from the service families 155, the onboard systems 160, and the onboard sensors 170 of Platform B (150) (preferably via the connection 183, described below), in addition to data, information, and requests from similar components on other platforms, such as Platform A (101) and Platform C (190) of FIG. 1 (preferably via the communication data link 140, described further below).

In addition, also in a preferred embodiment, the GDP 175 also facilitates the functions of the embedded health management systems of other platforms, such as the embedded health management system 130 of Platform A (101). For example, in one preferred embodiment, the GDP 125 collects and distributes pertinent data for the operation of the embedded health management system 130 of Platform A (101) from the service families 155, the onboard systems 160, the onboard sensors 170, and the embedded health management system 180 of Platform B (150) with the data linkage of the GDP 175 (preferably via the communication data link 140).

The connection 183 couples the service families 155, the onboard systems 160, the onboard sensors 170, the GDP 175, and the embedded health management system 180 of FIG. 1 to one another. In one exemplary embodiment, the connection 183 comprises a communications bus. In another exemplary embodiment, the connection 183 comprises a wireless network. In yet other exemplary embodiments, the connection 183 may comprise any one or more of a number of different types of connections.

Also in the depicted embodiment, Platform C (190) comprises various service families 195 and onboard systems 197, as well as a gateway data proxy (GDP) 199 configured as a stand-alone component for embedded health management system on the platform and a connection 193. For example, in one exemplary embodiment, Platform C (190) includes various service families 195 and onboard systems 197, as well as a gateway data proxy (GDP) 197 and a connection 193 each embedded on a particular vehicle, computer, and/or other type of device and/or system, such as a monitoring, command, and/or control unit or system responsible for Platform A (101) and Platform B (150), among other possible vehicles, computers, devices, and/or systems.

Platform C (190) may have any number of different service families 195 (also referred to herein as local service families for Platform C (190), and preferably comprising service family systems). The service families 195 may include indicative services. In a preferred embodiment, the service families 195 include monitoring or performing of such services for or pertaining to operation of various other platforms, such as Platform A (101) and Platform B (150) of FIG. 1.

Platform C (190) may also have any number of different onboard systems 197. The onboard systems 197 preferably each include one or more systems, computers, and/or devices that utilize information of the service families 195. In a preferred embodiment, the onboard systems 197 perform such system functions with respect to various other platforms, such as Platform A (101) and Platform B (150) of FIG. 1, for example in providing information for or pertaining to Platform A (101) and Platform B (150).

The GDP 199 resides on Platform C (190), and is coupled to the embedded health management systems of the other platforms. For example, in the depicted embodiment, the GDP 199 is coupled to the embedded health management system 130 of Platform A (101) and to the embedded health management system 180 of Platform B (150), and the like 180. The GDP 199 facilitates and leverages the functional capabilities of such embedded health management systems. For example, in one preferred embodiment, the GDP 199 collects data, information, and requests for the embedded health management system 130 of Platform A (101) and the embedded health management system 180 of Platform B (150), and from the service families 195 and the onboard systems 197 of Platform C (190), in addition to data, information, and requests from similar components of other platforms, such as Platform A (101) and Platform C (190) of FIG. 1 (preferably via the communication data link 140, described further below), and potentially from other possible platforms.

The connection 193 couples the service families 195, the onboard systems 197, and the GDP 199 to one another. In one exemplary embodiment, the connection 193 comprises a communications bus. In another exemplary embodiment, the connection 193 comprises a wireless network. In yet other exemplary embodiments, the connection 193 may comprise any one or more of a number of different types of connections.

The communication data link 140 couples the various platforms together, such as Platform A (101), Platform B (150), and Platform C (190) of FIG. 1. Specifically, in a preferred embodiment, the communication data link 140 couples the GDP 125 of Platform A (101), the GDP 175 of Platform B (150), and the GDP 199 of Platform C (190) of FIG. 1. In a preferred embodiment, the communication data link 140 comprises one or more different types of wireless networks.

Figure 2:
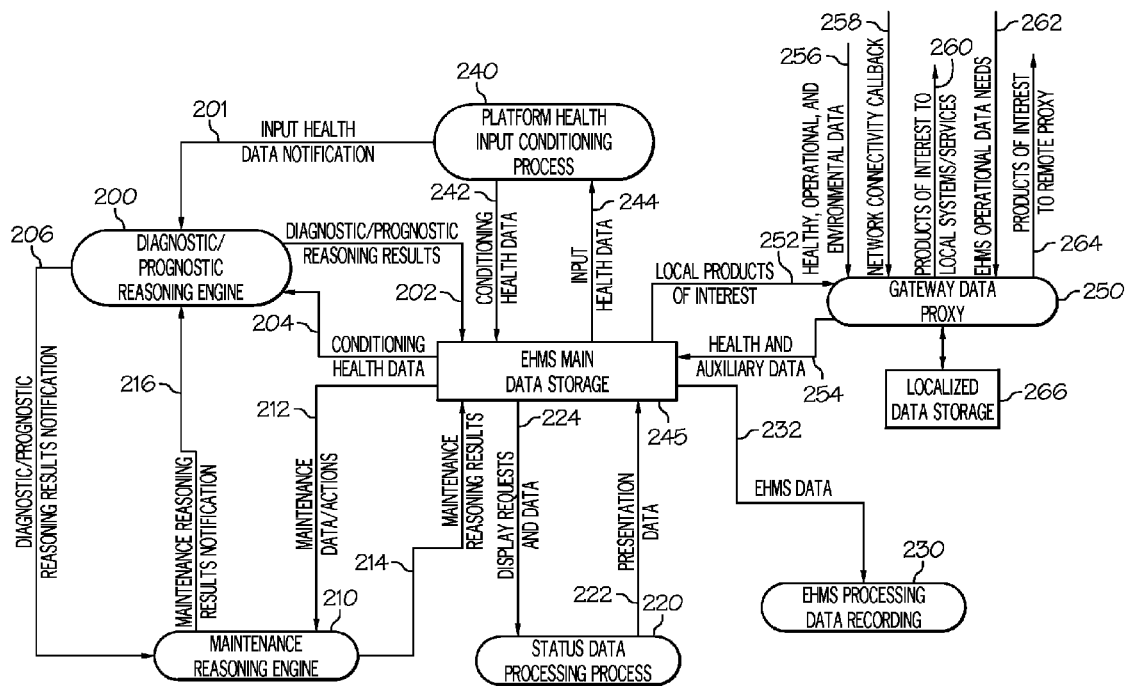
FIG. 2 is a flowchart depicting an interaction of an exemplary gateway data proxy of an exemplary platform of FIG. 1 with various sibling services of the exemplary platform, in accordance with an exemplary embodiment.

Turning now to FIG. 2, a flowchart depicting an interaction of an exemplary gateway data proxy (GDP) 250 of an exemplary platform of FIG. 1 with various sibling services of the exemplary platform, in accordance with an exemplary embodiment. For example, in one exemplary embodiment, the GDP 250 corresponds to the GDP 125 of Platform A (101) of FIG. 1, and the flowchart of FIG. 2 depicts an interaction of the DPD 125 of Platform A (101) of FIG. 1 with various sibling services 131 of Platform A (101) of FIG. 1. As another example, in another exemplary embodiment, the GDP 250 corresponds to the GDP 175 of Platform B (150) of FIG. 1, and the flowchart of FIG. 2 depicts an interaction of the GPD 175 of Platform B (150) of FIG. 1 with various sibling services 181 of Platform B (150) of FIG. 1.

In the embodiment depicted in FIG. 2, the interaction between the GDP 250 and the sibling services includes a platform health input conditioning process 240, embedded health management system (EHMS) data storage 245, a diagnostic and prognostic reasoning engine 200, a maintenance reasoning engine 210, a status data presenting process 220, an EHMS processing data recording 230, and localized data storage 266.

In a preferred embodiment, the interaction is initiated by providing an offer for health status results, maintenance status and records, platform readiness, and other health related data generated by local EHMS 130 and 180 in FIG. 1, and by processing the requests from the sibling services for supportive data products produced by other service families and/or systems from a same platform or a remote platform 252 for the GDP 250. Also in a preferred embodiment, as the result of one or more such requests for data of interest 252 pertaining to data or information needed to support the operation, maintenance and/or health assessment of the respective platform, GDP 250 acquires and stores the indicative data 254 in the EHMS data storage 245. In response to the requests of sibling services and other requests for data of interest from local service families 263, the GDP sends requests for corresponding data of interest 260 (such as operational, health, usage data, environmental data, mode status information, maintenance orders and records, supply data, equipment and platform readiness, diagnostics and/or prognostics results pertaining to the operation and/or health of the respective platform) to local systems and/or services on the same platform as well as other corresponding data of interest 264 to remote GDPs on other platforms (such as operational, health, usage data, environmental data, mode status of individual piece of equipment and platform, maintenance orders and records, diagnostics and/or prognostics results pertaining to the operation and/or health of the a remote platform) in order to obtain the requested data and information.

The GDP 250 then receives, in response to these requests, health, operational, maintenance orders and records, environmental data from the same platform as well as from other platforms 256. For the network connectivity status, if there is a loss in connectivity, the GDP 250 receives this information via a network connectivity call-back 258. In addition, the GDP 250 preferably also receives EHMS operational data needs from one or more embedded health management systems (EHMS), and from other systems and service families on the same platform 262. The various data and information received by the GDP 250 are preferably stored in localized data storage 266 to support various deployment configurations of the GDP 250, and depending on the need of sibling services, the GDP 250 places the equipment health related data and auxiliary data 254 to the EHMS data storage 245 to allow the EHMS performing its operations.

Input health data 244 is then provided for the platform health input conditioning process 240. In a preferred embodiment, the input health data corresponds to the heath and auxiliary data 254 provided by the GDP 250, and includes data pertaining to the health and/or operation of the platform on which the GDP 250 resides, as well as relevant data pertaining to other platforms with which the GDP 250 has shared information.

The input health data 244 is then filtered, conditioned, and transformed during the platform health input condition process 240 of the EHMS. Specifically, the input health data 244 is processed by the respective embedded health management system (EHMS) of the respective platform for use by the EHMS during the platform health input conditioning process 240. In addition, the resulting conditioning health data 242 is provided to the EHMS data storage 245, and an input health data notification or trigger 201 is provided to the diagnostic and prognostic reasoning engine 200.

The diagnostic and prognostic reasoning engine 200 of the EHMS obtains stored conditioning health data 204 from the EHMS main data storage 245 after receiving the notification 201 from the platform health input conditioning process 240. The diagnostic and prognostic reasoning engine 200 processes the stored conditioning health data 204 and generates diagnostic and prognostic reasoning results 202. The diagnostic and prognostic reasoning results 202 are provided to the EHMS data storage 245, and a notification 206 pertaining thereto is provided to the maintenance reasoning engine 210 to initiate the maintenance activity process by the diagnostic and prognostic reasoning engine 200.

Upon receiving the notification 206 from the diagnostic and prognostic reasoning engine 200, the maintenance reasoning engine 210 of the EHMS obtains maintenance data and actions 212 from the EHMS data storage 245 based on the diagnostic and prognostic reasoning results 202. The maintenance reasoning engine 210 processes this data and information in order to generate maintenance reasoning results 214. The maintenance reasoning results 214 are provided to the EHMS data storage 245, and a notification 216, results of maintenance activities is provided to the diagnostic and prognostic reasoning engine 200 for further processing and for use in updating the diagnostic and prognostic reasoning results 202.

The status data presenting process 220 of the EHMS receives display requests and data 224 from the EHMS data storage 245. In a preferred embodiment, the display requests pertain to one or more requests for displays of information pertaining to the diagnostic and prognostic reasoning results 202 and/or the maintenance reasoning results 214. The display request may be made, by way of example only, from one or more platforms, computer systems, operators, control centers, users, and/or other individuals, devices, and/or systems, by way of further example.

The status data presenting process 220 then prepares presentation data 222 based on the display request and data 224. The presentation data 222 may include, by way of example only, diagnostic and prognostic results, maintenance records and recommendations, operational data and characteristics of the corresponding platform and/or one or more other platforms, and/or various other types of presentation data 222. The presentation data 222 is preferably displayed on one or more audio and/or visual displays. In addition, the presentation data 222 is preferably stored in the EHMS data storage 245 (to allow the GDP 250 to distribute the presentation data 222 to a display service family of the platform) and sent to the EHMS data recording device 230 as EHMS data 232 to be recorded along with other data extraction from EHMS data storage 245 for subsequent use for operational playback and performance accuracy analysis of the EHMS.

Figure 3:
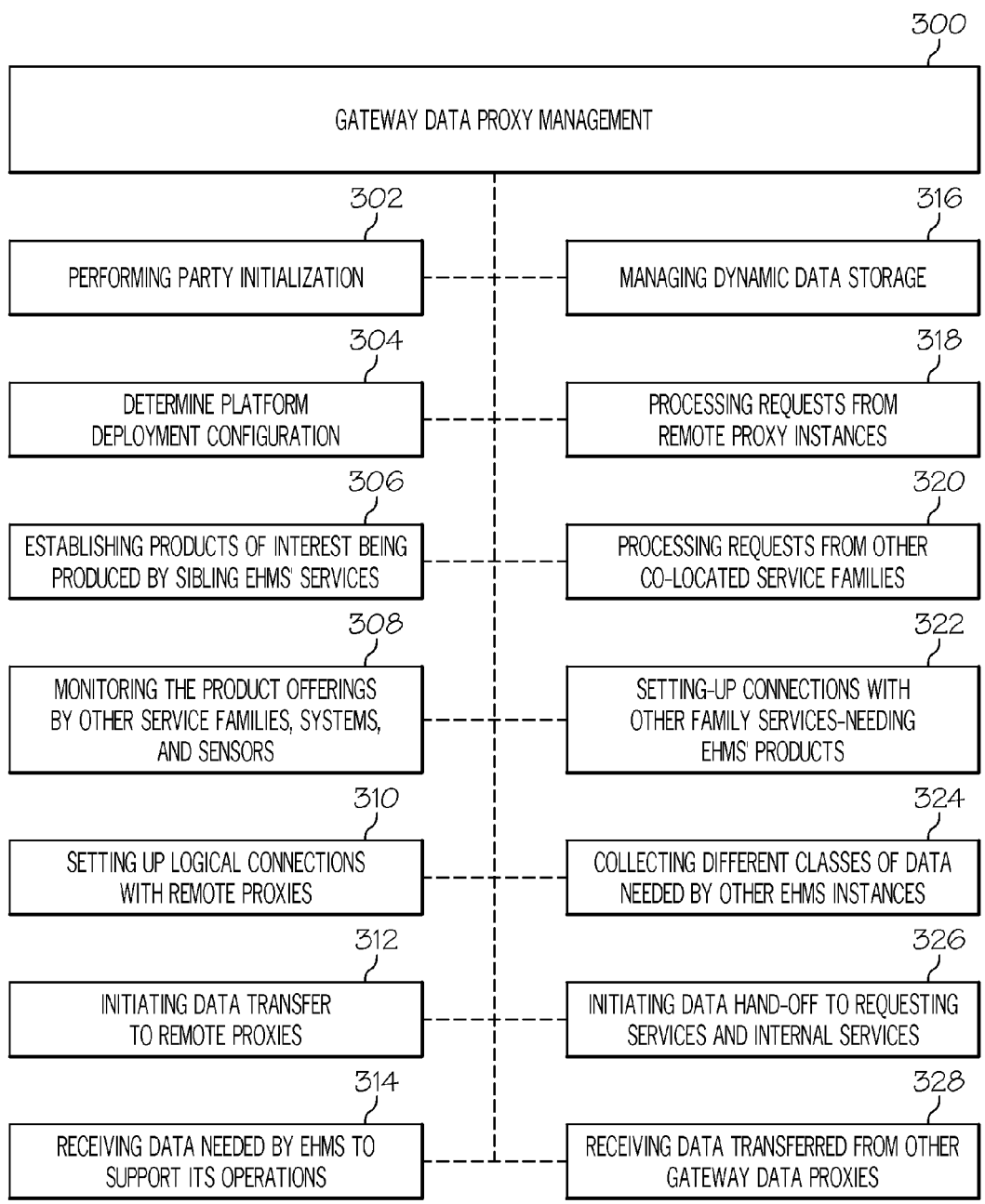
FIG. 3 is a flowchart depicting a composite management structure of an exemplary gateway data proxy of an exemplary platform of FIG. 1, in accordance with an exemplary embodiment.

FIG. 3 is a flowchart depicting a composite management structure 300 of an exemplary gateway data proxy (GDP) of an exemplary platform of FIG. 1, in accordance with an exemplary embodiment. In a preferred embodiment, the composite management structure 300 is used for the GDP 250 of FIG. 2. In addition, in one preferred embodiment, the composite management structure 300 is used for each of the GDP 125 of Platform A (101) of FIG. 1, the GDP 175 of Platform B (150) of FIG. 1, and the GDP 199 of Platform C (190) of FIG. 1.

As depicted in FIG. 3, the GDP performs proxy initialization of data (302) for one or more platforms, for example for data that may include requests or information pertaining to one or more services or products, and/or relating to operation or health of one or more of the platforms. In addition, the GDP determines its role and associated functional capabilities based on the data setup as part of deployment configuration (304). The GDP also establishes products of interest (such as data, information, results, determinations, diagnostics, and/or prognostics, maintenance record, maintenance status pertaining to the operation and/or health of the respective platform) being produced and maintained by sibling EHMS services (306) that are embedded within the EHMS. The GDP also monitors the product offerings by other service families, systems, and sensors on the platform (308) (such as data and/or information pertaining to the operation and/or health of the respective platform as provided by such service families, systems, and sensors).

In addition, the GDP also sets up logical connections with remote gateway data proxies (also referred to herein as proxies) on other platforms (310) and initiates bi-directional data exchange with remote proxies (312). The GDP also receives data needed by a respective platform EHMS to support its operations (314), for example in determining health characteristics of one or more platforms. The GDP also preferably manages dynamic data storage (316), processes requests from remote gateway data proxies from other platforms (318), and processes requests from other co-located service families (320).

Also in the depicted embodiment, the GDP establishes connections with other family services that require products or data from the platform EHMS (322). The GDP also collects different classes of data that are needed by EHMS services on other platforms that are coupled through the GDP (324). In addition, the GDP initiates data supply to any sibling services and/or service families that may require or request such data (326), and receives data that is transferred from other gateway data proxies (GDPs) resided on other platforms (328).

Figure 4:
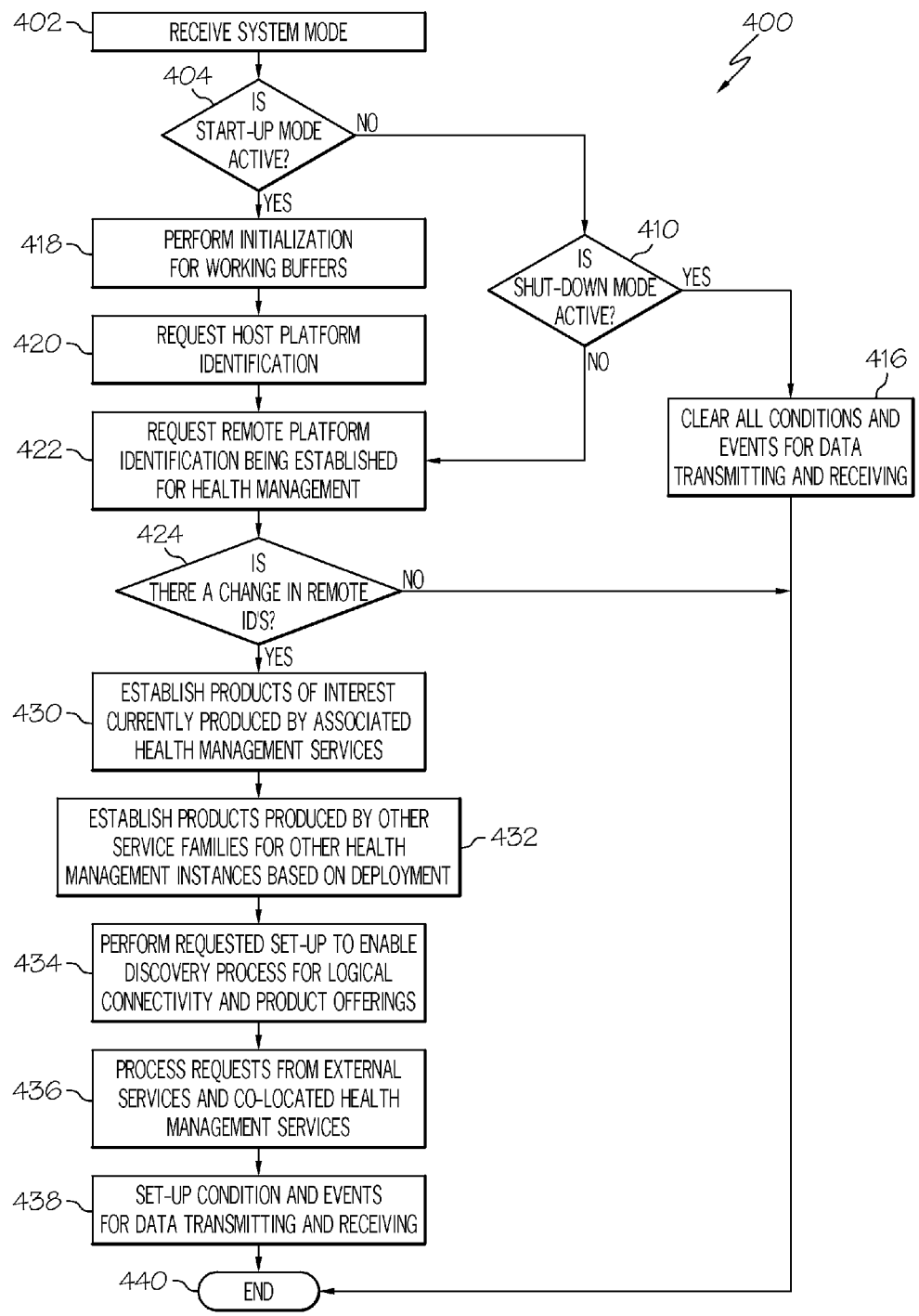
FIG. 4 is a flowchart depicting a process for data health management, and that can be used in connection with the system of FIG. 1 or in connection with an exemplary gateway data proxy of an exemplary platform of FIG. 1, in accordance with an exemplary embodiment.

Turning now to FIG. 4, a flowchart is provided for a gateway data proxy management process 400 for data health management using a gateway data proxy (GDP), in accordance with an exemplary embodiment. In a preferred embodiment, the gateway data proxy management process 400 can be utilized in connection with the system 100 of FIG. 1, and in connection with the GDP 250 of FIG. 2, the GDP 125 of Platform A (101) of FIG. 1, the GDP 175 of Platform B (150) of FIG. 1, and the GDP 199 of Platform C (190) of FIG. 1.

As depicted in FIG. 4, the gateway data proxy management process 400 begins in an exemplary embodiment with the step of receiving a system mode notification (step 402). A determination is then made as to whether the system mode is an active start-up mode (step 404).

If a determination is made in step 404 that the system mode is an active start-up mode, then initialization is performed for working buffers (step 418). A request for host platform identification is then made (step 420), and a request for remote platform identification is then established for health management for respective platforms (step 422).

A determination is then made as to whether there is a change in remote platform identification (step 424). If it is determined in step 424 that there is no change in remote identification (for example, if the platform identification corresponds to an existing platform that the GDP is already functioning with), then the process terminates (step 440).

Conversely, if it is determined in step 424 that there is a change in remote platform identification (for example, if the platform identification corresponds to a new or different platform that the GDP is not currently functioning with), then the GDP establishes products of interest (e.g., areas of data and/or processing of interest to the newly associated platform) that are currently produced by sibling health management services for a newly established platform (step 430). In addition, the GDP establishes indicative products produced by other local service families for other health management systems based on deployment setup on the respective platforms (step 432).

In addition, the GDP performs required setup to enable discovery processes for logical connectivity and product offerings for the respective platforms (step 434). The GDP also processes requests for data of interest from external services and co-located health management services of the respective platforms (step 436). In addition, the GDP sets up conditions and events for data transmitting and receiving, for example to one or more embedded health management systems of one or more respective platforms that require or utilize such data and results based on data change or periodic (step 438). The process then terminates (step 440).

Returning now to step 404, if a determination is made during step 404 that the system mode does not represent a start-up mode, then a determination is made as to whether a shut-down mode is active (step 410). If a determination is made in step 410 that the shut-down mode is active, then all conditions and events for data transmitting and receiving are cleared (step 416), and the process then terminates (step 440). Conversely, if a determination is made in step 410 that the shut-down mode is not active, then the process instead returns to step 422, and steps 422-438 are then executed before the process terminates (step 440).

Figure 5A:
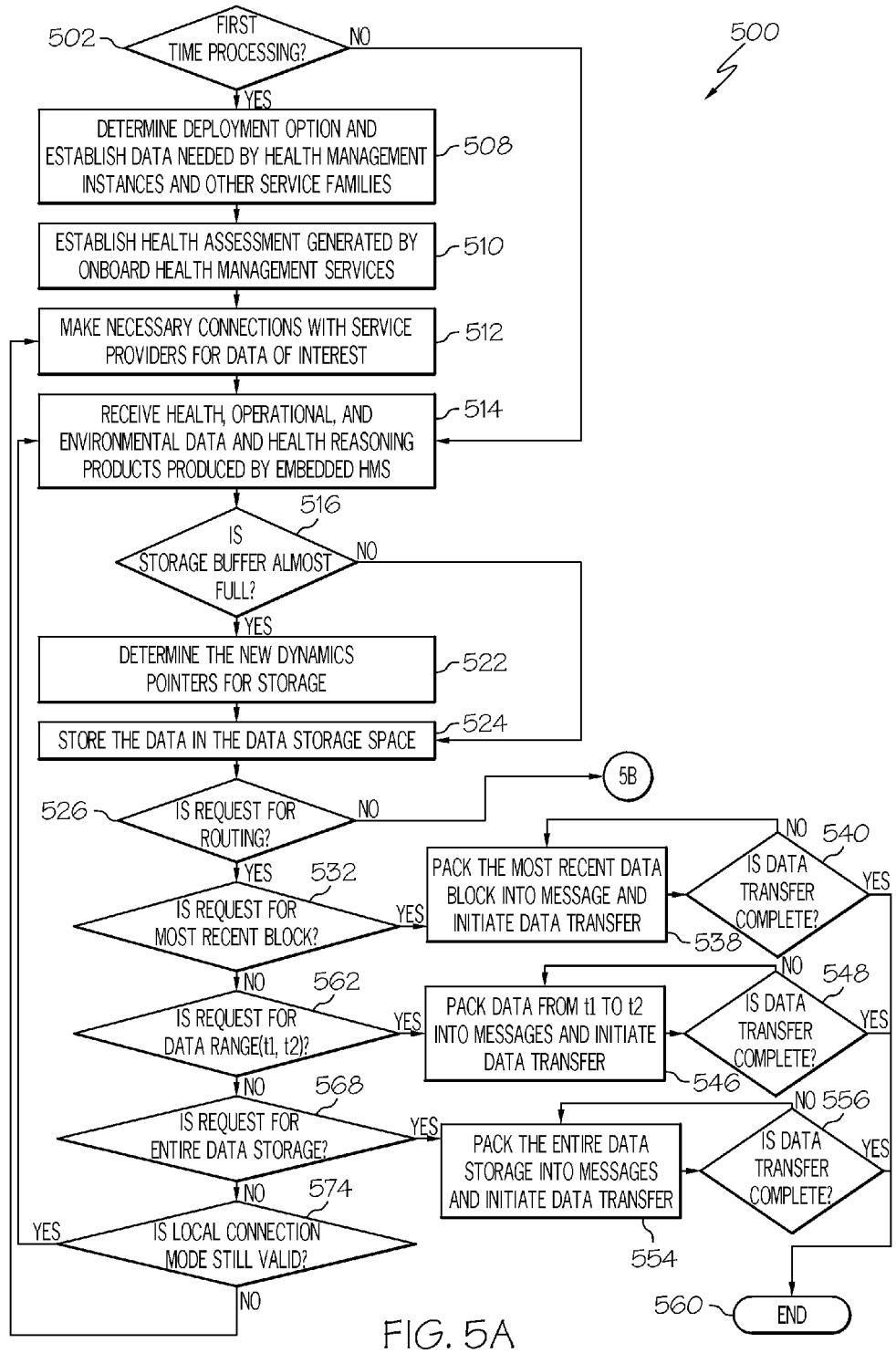
FIGS. 5A and 5B comprise a flowchart depicting another process for data health management, and that can be used in connection with the system of FIG. 1 or in connection with an exemplary gateway data proxy of an exemplary platform of FIG. 1, in accordance with an exemplary embodiment.
Figure 5B:
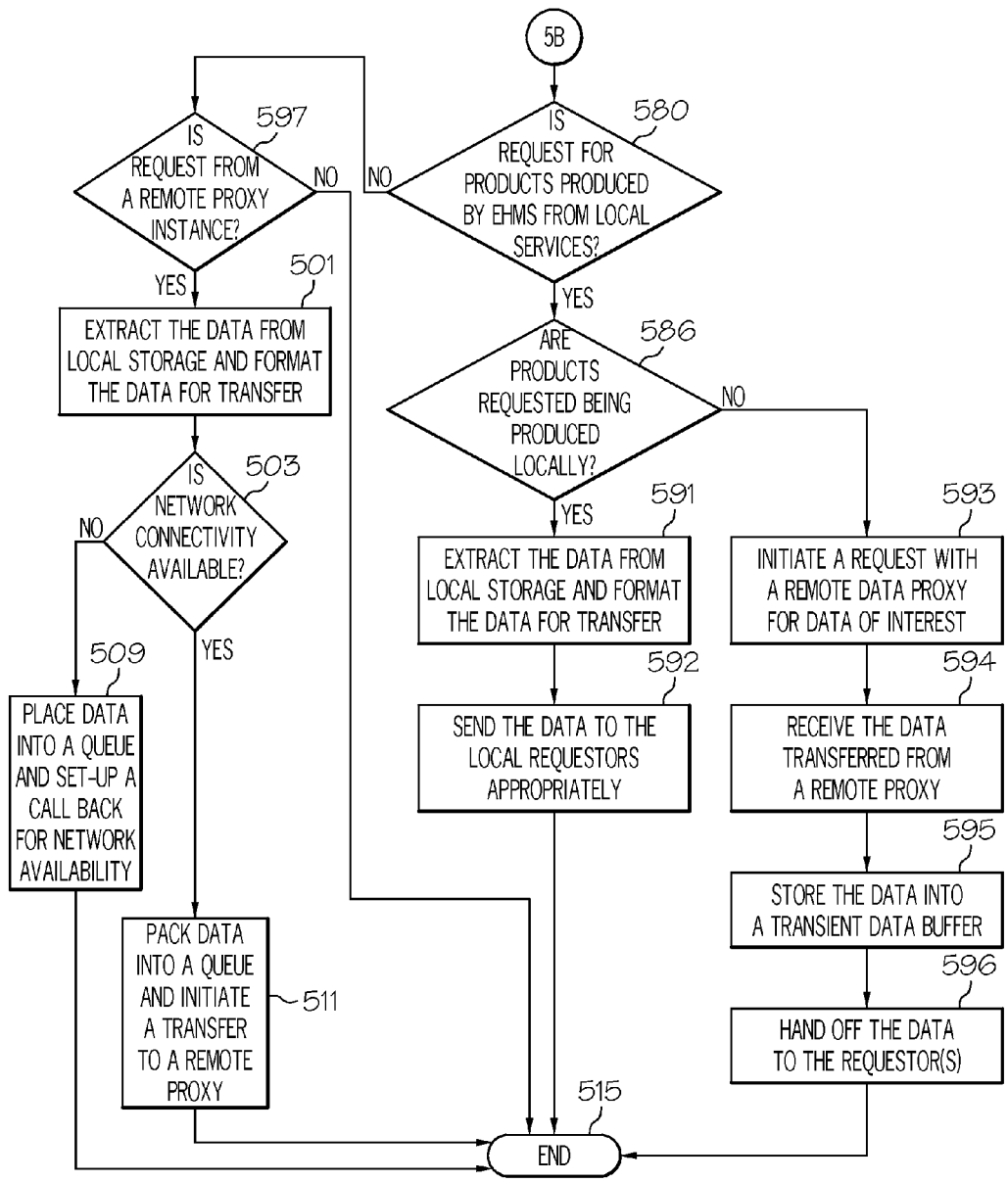

FIGS. 5A and 5B comprise a flowchart depicting a data health management process 500 for data health management using a gateway data proxy and one or more embedded health management systems, in accordance with an exemplary embodiment. In a preferred embodiment, the steps are performed by a gateway data proxy, and most preferably by a processor thereof. In a preferred embodiment, the data health management process 500 can be utilized in connection with the gateway data proxy management process 400 of FIG. 4, the system 100 of FIG. 1, and in connection with the GDP 250 of FIG. 2, the GDP 125 of Platform A (101) of FIG. 1, the GDP 175 of Platform B (150) of FIG. 1, and the GDP 199 of Platform C (190) of FIG. 1.

As depicted in FIG. 5, the data health management process 500 begins with the step of determining whether a current loop or iteration represents a first time processing of the data (step 502). If a determination is made in step 502 that the current loop or iteration does not represent a first time processing of the data, then the process jumps to step 514, described further below. Conversely, if a determination is made in step 502 that the current loop or iteration represents a first time processing of the data, then the process instead proceeds to step 508, described directly below.

During step 508, a determination is made as to a deployment option, and data is established that is needed by health management instances on other platforms and other service families. In addition, health assessments are established and generated by health management services and obtained thereof by the GDP (step 510). The GDP then establishes necessary connections for service providers for data of interest that may be needed for on-going processing and generation of health determinations, results, maintenance requests, diagnostics, and/or prognostics (step 512).

Next, during step 514, the GDP receives health, operational, and environmental data and health reasoning products, data, and/or results that are produced by one or more platform embedded health management systems (EHMS). In addition, a determination is made as to whether the storage buffer is almost full (step 516). For example, in one exemplary embodiment, the storage buffer is deemed to be almost full if the storage buffer is about seventy-five percent full. However, this may vary in other embodiments, for example as different threshold values may be used.

If a determination is made during step 516 that the storage buffer is not almost full, then the process skips to step 524, described further below. Conversely, if a determination is made during step 516 that the storage buffer is almost full, then the process proceeds instead to step 522, described directly below. During step 522, the GDP determines new dynamic pointers for storage. Next, in step 524, the GDP stores the data in the data storage space.

Next, a determination is made by the GDP whether there has been a request for routing of information (step 526). If it is determined during step 526 that there has been a request for routing of information, then a determination is made as to whether a request for a most recent block of information has been made (step 532).

If it is determined during step 532 that a request for a most recent block of information has been made, then the process proceeds to step 538, in which the most recent data block is packed into a message, and data transfer is initiated via transfer of the message to one or more services and/or other platform entities requesting the data. Following step 538, a determination is made as to whether data transfer is complete (step 540). If a determination is made in step 540 that data transfer is complete, then the process terminates (step 560). Conversely, if a determination is made in step 540 that data transfer is not complete, then the process returns to step 538, as step 538 repeats with the packing of new, most recent data blocks into messages and data transfer continues until there is a determination in a subsequent iteration of step 540 that data transfer is complete.

Returning now to step 532, if a determination is made in step 532 that a request for a most recent block of information has not been made, then the process proceeds to step 562. In step 562, a determination is made as to whether a request for a data within range (t1, t2) (for example, data within a requested time period) has been made.

If it is determined in step 562 that a request for a data within range (t1, t2) has been made, then the process proceeds to step 546. During step 546, data from the requested data range (t1, t2) is packed into a message, and data transfer is initiated via transfer of the message to one or more services and/or other platform entities requesting the data. Following step 546, a determination is made as to whether data transfer is complete (step 548). If a determination is made in step 548 that data transfer is complete, then the process terminates (step 560). Conversely, if a determination is made in step 548 that data transfer is not complete, then the process returns to step 546, as step 546 repeats with packing of new data from the data within range (t1, t2) (for example, data within one or more new requested time periods), and data transfer continues until there is a determination in a subsequent iteration of step 548 that data transfer is complete.

Returning now to step 562, if a determination is made in step 562 that a request for a data within range (t1, t2) has not been made, then the process proceeds to step 568. During step 568, a determination is made as to whether a request for entire data storage has been made.

If it is determined in step 568 that a request for entire data storage has been made, then the process proceeds to step 554. During step 554, the entire data is packed into messages, and data transfer is initiated via transfer of the message to one or more services and/or other platform entities requesting the data. Following step 554, a determination is made as to whether data transfer is complete (step 556). If a determination is made in step 556 that data transfer is complete, then the process terminates (step 560). Conversely, if a determination is made in step 560 that data transfer is not complete, then the process returns to step 554, as step 554 repeats with packing of the entire data storage in messages and data transfer continues until there is a determination in a subsequent iteration of step 556 that data transfer is complete.

Returning now to step 568, if a determination is made in step 568 that a request for entire data storage has not been made, then the process proceeds to step 574. During step 574, a determination is made as to whether a local connection mode is still valid with respect to a connection between the GDP and any applicable other gateway data proxies, embedded health management system, services, platforms, and/or other devices and/or systems.

If it is determined in step 574 that a local connection mode is still valid, then the process returns to the above-referenced step 514, as additional health, operational, and environmental data are received and additional health reasoning products and produced by an embedded health management system coupled to the GDP and the process continues from step 514 as referenced above. Conversely, if it is determined in step 574 that a local connection mode is not valid, the process returns instead to the above-referenced step 512, as necessary, connections are established with service providers for data of interest, and the process continues from step 512 as referenced above.

Returning now to step 526, if a determination is made in step 526 that a request for routing has not been made, then the process proceeds to step 580 of FIG. 5 B. During step 580, a determination is made as to whether a request has been made for products or information (such as data, information, results, determinations, diagnostics, and/or prognostics pertaining to the operation and/or health of the respective platform) produced by an embedded health management system (EHMS) from one or more sibling services.

If it is determined in step 580 that a request has been made for products or information produced by an embedded health management system (EHMS) for one or more local services, then the process proceeds to step 586. During step 586, a determination is made as to whether there have been any requests to produce products locally within a respective platform.

If it is determined in step 586 that there have been one or more requests to products produced locally within a respective platform, then the process proceeds to step 591. During step 591, data is extracted from local storage, and the data is formatted for transfer. Following step 591, the data is sent to the local requestors (step 592). The process then terminates (step 515).

Conversely, if it is determined in step 586 that there have been no requests to products produced locally within a respective platform, then the process proceeds instead to step 593. During step 593, a request is initiated with a remote gateway data proxy of another platform for data of interest. Following step 593, the GDP receives data that has been transferred or provided from a remote gateway data proxy from another platform (step 594). The data is then stored into a transient data buffer (step 595). In addition, the data is also provided to the one or more requestors (step 596). The process then terminates (step 515).

Returning now to step 580, if it is determined in step 580 that a request has not been made for products or information produced by an embedded health management system (EHMS) for one or more local services, then the process proceeds to step 597. During step 597, a determination is made as to whether there have been any requests have been made from any remote proxies from another platform. If a determination is made during step 597 that there have not been any remote proxies made from another platform, then the process terminates (step 515).

Conversely, if a determination is made during step 597 that there have been one or more remote proxies made from another platform, then the process instead proceeds to step 501. During step 501, data is extracted from local storage, and the data is formatted for transfer. Following step 501, a determination is made as to whether network connectivity is available (preferably via the communication data link 140 of FIG. 1) (step 503).

If it is determined in step 503 that network connectivity is available, then the process proceeds to step 511. During step 511, the data is packed into a queue, and data transfer is initiated to a remote gateway data proxy on another platform. The process then terminates (step 515).

Conversely, if it is determined in step 503 that network connectivity is not available, then the process proceeds instead to step 509. During step 509, the data is placed into a queue, and a callback is initiated requested network availability, and preferably also for notification of when the network connectivity is available. The process then terminates (step 515).

Figure 6:
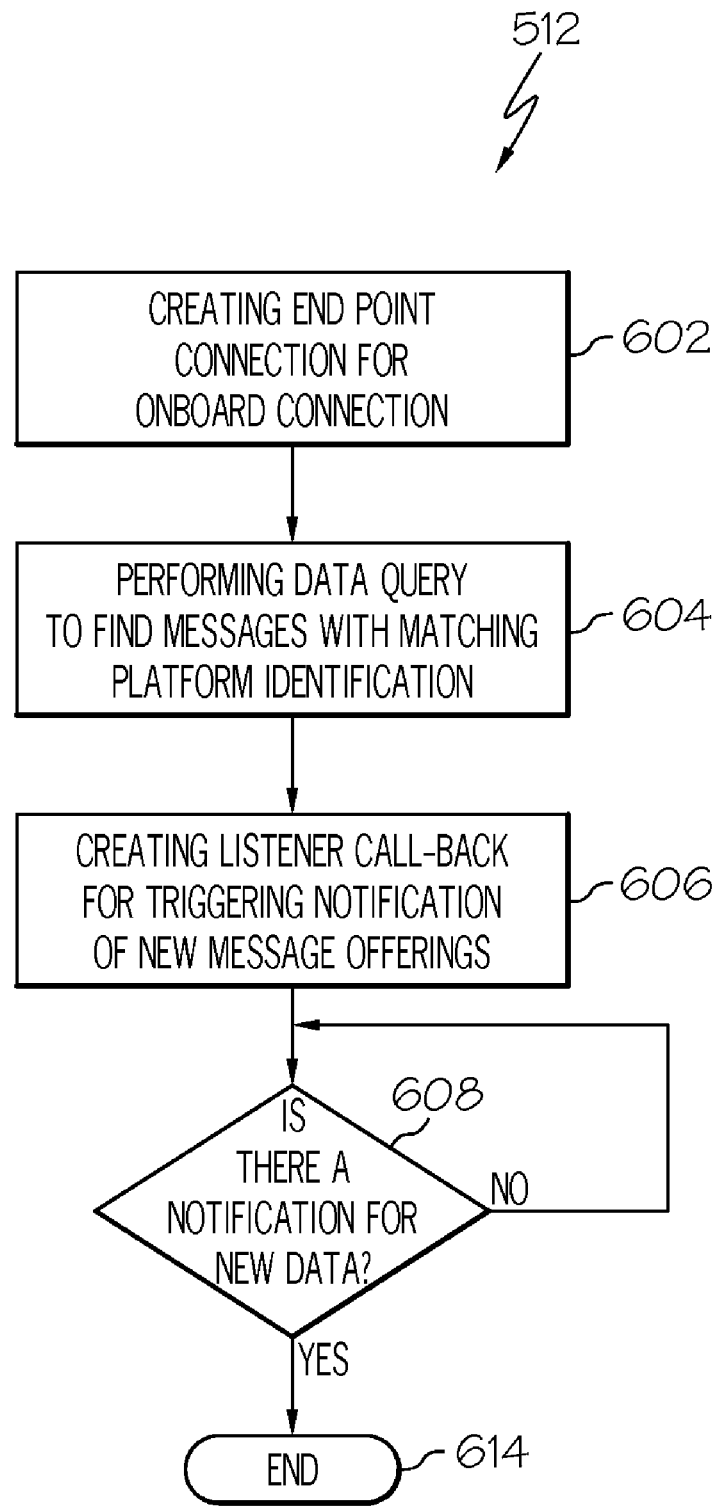
FIG. 6 is a flowchart depicting a first embodiment of a step of the process of FIGS. 5A and 5B, namely the step of establishing connections with service providers for data of interest, and that can be used in connection with the system of FIG. 1 or in connection with an exemplary gateway data proxy of an exemplary platform of FIG. 1, in accordance with an exemplary embodiment.

FIG. 6 is a flowchart depicting a first embodiment of a step of the process of FIGS. 5A and 5B, namely the step of establishing connections with service providers for data of interest (step 512 of FIGS. 5A and 5B), in accordance with an exemplary embodiment. In the first embodiment of FIG. 6, step 512 of FIGS. 5A and 5B begins with creating an end-point connection for onboard connection for the platform on which the GDP resides (step 602).

The GDP also performs a data query in order to find messages with matching platform identifications (step 604). In addition, the GDP creates listener call-back for triggering notification of any new message offerings (step 606).

The GDP also performs a determination as to whether there is a notification for new data (step 608). If a determination is made during step 608 that there is no notification for new data, then the process returns to step 608. Step 608 repeats until there is a determination in an iteration of step 608 that there is a notification for new data. Once there is a determination in an iteration of step 608 that there is a notification for new data, then the process terminates (step 614).

Figure 7:
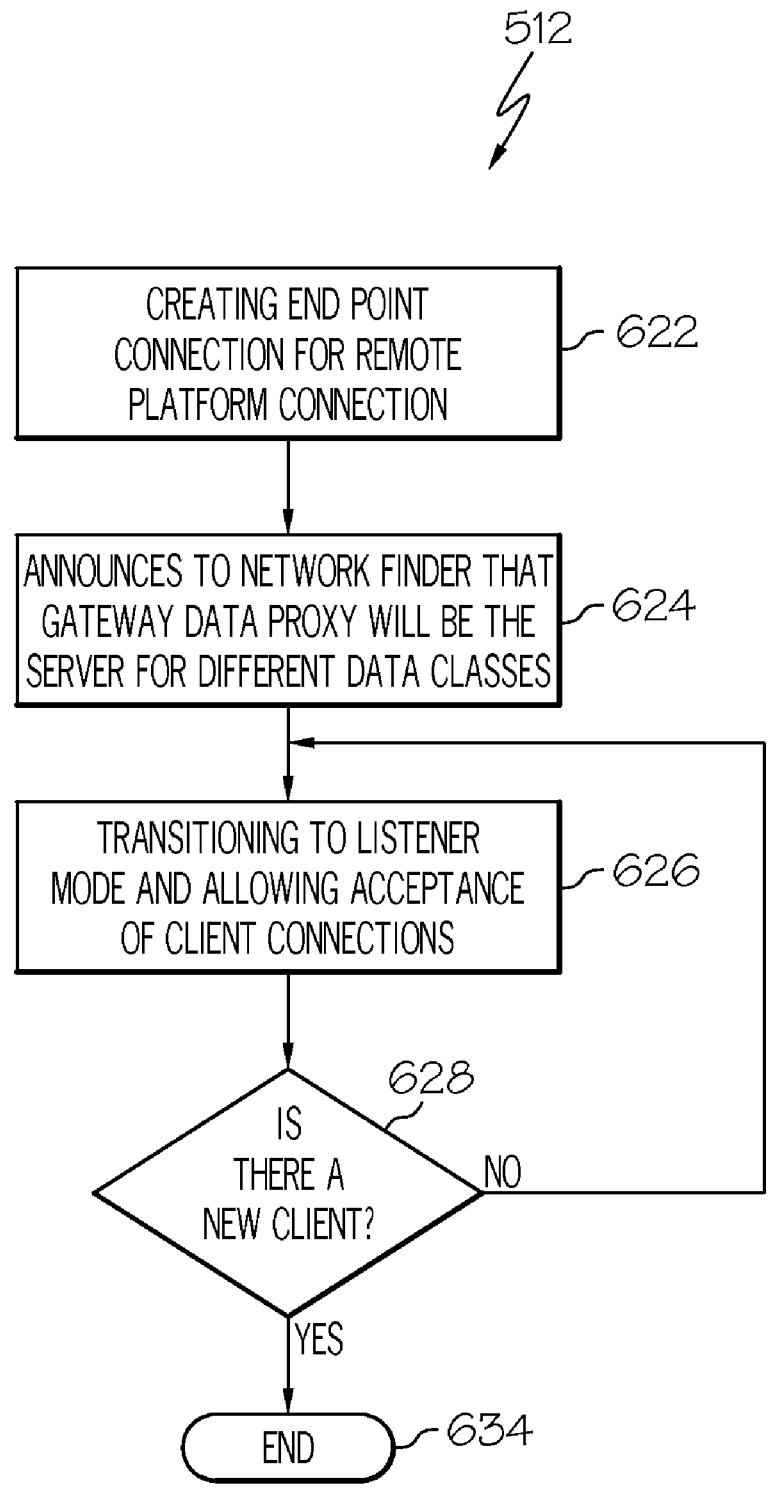
FIG. 7 is a flowchart depicting a second embodiment of a step of the process of FIGS. 5A and 5B, namely the step of establishing connections with service providers for data of interest, and that can be used in connection with the system of FIG. 1 or in connection with an exemplary gateway data proxy of an exemplary platform of FIG. 1, in accordance with an exemplary embodiment.

FIG. 7 is a flowchart depicting a second embodiment of a step of the process of FIGS. 5A and 5B, namely the step of establishing necessary connections with service providers for data of interest (step 512 of FIGS. 5A and 5B), in accordance with an exemplary embodiment. In the second embodiment of FIG. 7, step 512 of FIGS. 5A and 5B begins with creating an end-point connection for remote platform connection on another platform other than the platform on which the GDP resides (step 622).

The GDP also announces to a network finder that the GDP will be the server for different data classes (step 624). In addition, the GDP transitions to a listener mode, and allows the acceptance of client connections (step 626). In a preferred embodiment, the client connections corresponds to connections with one or more services, health management systems, controllers, computers, individuals, devices, and/or systems making requests for data of interest.

The GDP also performs a determination as to whether there is a new client, for example that is requesting information, data, results, determinations, diagnostics, and/or prognostics from the GDP (step 628). If a determination is made during step 628 that there is a new client, then the process returns to step 628. Step 628 repeats until there is a determination in an iteration of step 628 that there is a new client. Once there is a determination in an iteration of step 628 that there is a new client, then the process terminates (step 634).

Figure 8:
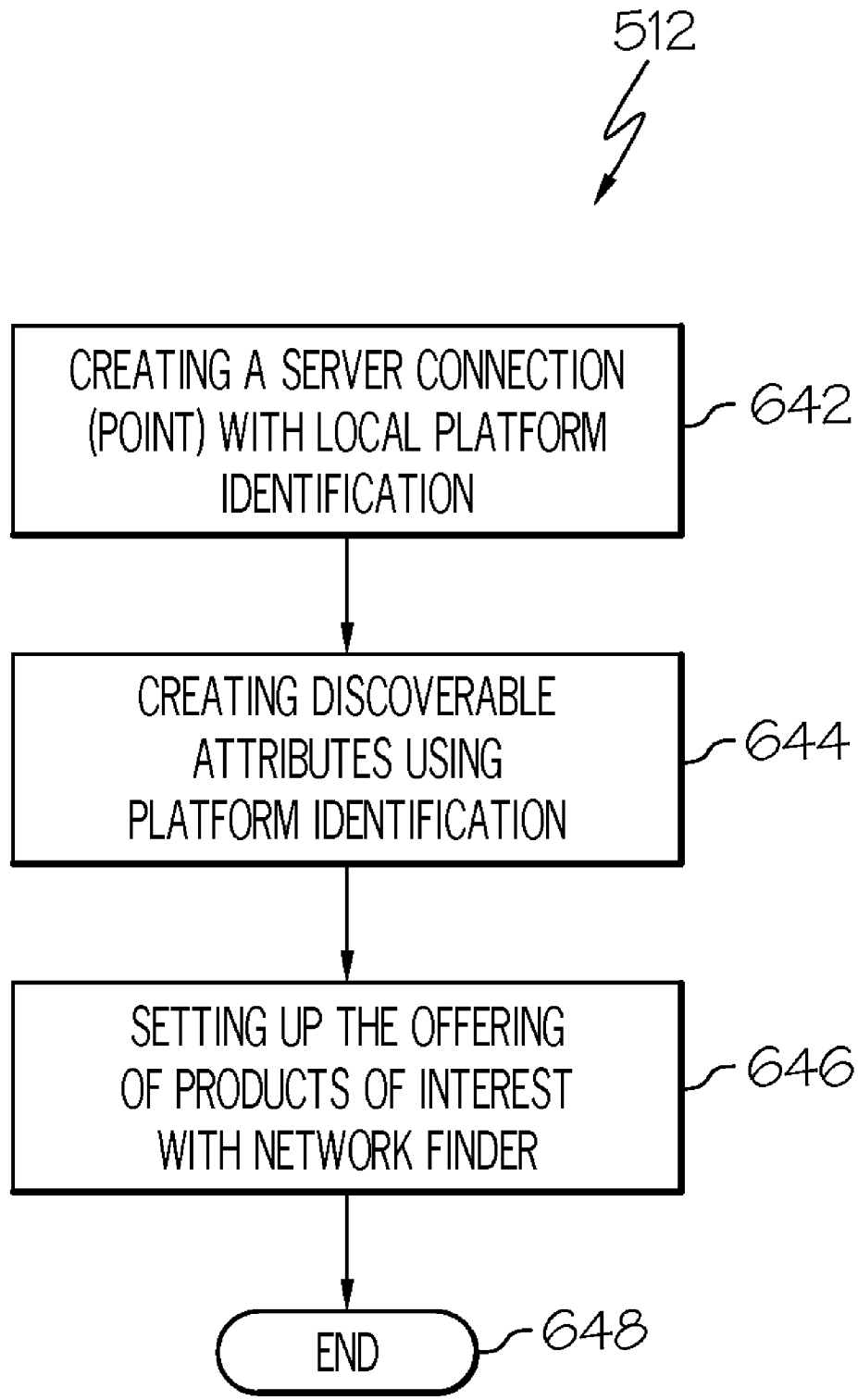
FIG. 8 is a flowchart depicting a third embodiment of a step of the process of FIGS. 5A and 5B, namely the step of establishing connections with service providers for data of interest, and that can be used in connection with the system of FIG. 1 or in connection with an exemplary gateway data proxy of an exemplary platform of FIG. 1, in accordance with an exemplary embodiment.

FIG. 8 is a flowchart depicting a third embodiment of a step of the process of FIGS. 5A and 5B, namely the step of establishing necessary connections with service providers for data of interest (step 512 of FIGS. 5A and 5B), in accordance with an exemplary embodiment. In the third embodiment of FIG. 8, step 512 of FIGS. 5A and 5B begins with creating a server connection or point with local platform identification (step 642). The GDP also creates discoverable attributes for the data using the platform identification (step 644). In addition, the GDP initiates an offering of data of interest (e.g., requested data, information, results, prognostics, diagnostics, analysis, and recommendations) with the network finder (step 646). The process then terminates (step 648).

Figure 9:
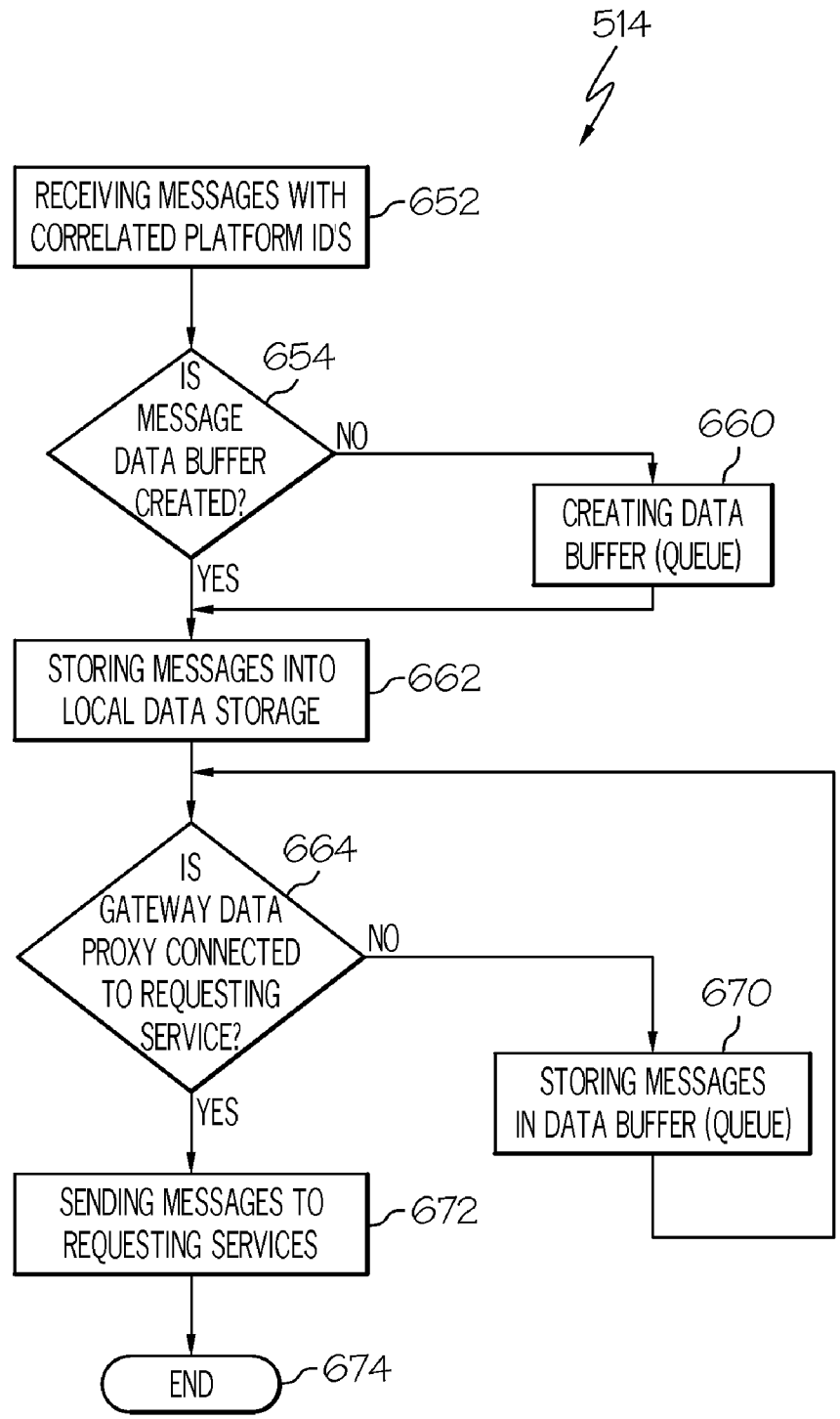
FIG. 9 is a flowchart depicting an exemplary embodiment of another step of the process of FIGS. 5A and 5B, namely the step of receiving health, operational, and environmental data and health reasoning products produced by an embedded health maintenance system, and that can be used in connection with the system of FIG. 1 or in connection with an exemplary gateway data proxy of an exemplary platform of FIG. 1, in accordance with an exemplary embodiment.

FIG. 9 is a flowchart depicting an exemplary embodiment of another step of the process of FIGS. 5A and 5B, namely the step of receiving health, operational, and environmental data and health reasoning products produced by an embedded health maintenance system (step 514), in accordance with an exemplary embodiment. As depicted in FIG. 9, in this embodiment step 514 of FIGS. 5A and 5B begins with the step of receiving one or more messages with correlated platform identifications (IDs) (step 652). A determination is then made as to whether a message buffer has been created (step 654).

If it is determined in step 654 that a message buffer has already been created, then the process proceeds to step 662. During step 662, messages are stored into local data storage by the GDP. For example, in one exemplary embodiment, during 662, the GDP 250 of FIG. 2 stores the messages into the localized data storage 266 of FIG. 2.

Conversely, if it is determined in step 654 that a message buffer has not yet been created, then a data buffer is created, and a queue is established for the messages (step 660). The process then proceeds to the above-referenced step 662, and messages are stored into local data storage by the GDP.

Following step 662, a determination is made as to whether the GDP is successfully connected to requestor(s) that could be another GDP on another platform or a communication service of a local service family (step 664). If a determination is made in step 664 that the GDP is connected to a requesting service, then the GDP sends the data of interest in a conforming data format to the requesting services (step 672), and thereby provides the requested data to the requestor via the messages.

Conversely, if a determination is made in step 664 that the GDP is not connected to a requesting service, then the GDP instead stores the messages in a queue (step 670) in accordance with the data buffer established in step 660. The process then returns to step 664, and a determination is made in a new iteration of step 664 as to whether the GDP is connected to a requesting service at a new point in time. Steps 664 and 670 repeat in this manner until a determination is made in a subsequent iteration of step 664 that the GDP is connected to a requesting service, at which point the GDP sends the messages to the requesting service in the above-described step 672.

Accordingly, improved systems and methods are provided for health monitoring for various platforms, such as vehicles. For example, the improved systems and methods utilize all available data, including platform operational data, environmental data, equipment health data, and data from remote platforms, in providing detailed health assessment in terms of various levels of platform availability and readiness with the facilitation of the gateway data proxies (GDPs).

It will be appreciated that the steps in the various processes depicted in the Figures and/or described above may vary, may be executed simultaneously, and/or may be executed in a different order than depicted in the Figures and/or described above. It will similarly be appreciated that various apparatus, devices, systems, interactions, relationships, management, and/or other features, and/or parts and/or components thereof, may vary from those depicted in the Figures and/or described above. It will also be appreciated that the methods and systems may be implemented in connection with any number of different types of land vehicles, aircraft, spacecraft, marine vehicles, other types of vehicles, computers, controllers, control centers, operators, devices, systems, modules, and/or any number of other different types of platforms.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

We claim:

1. A system comprising:
a first processor embedded within a first health management system residing on a first platform of a plurality of platforms and dynamically configured and established to obtain first data pertaining to operation of the first platform from the first health management system and to offer the first data and first generated products for offerings from each of a plurality of sibling service on a discoverable communication network; and
a second processor embedded as a scalable health management system with a single service on a second platform of the plurality of platforms and dynamically configured and established to obtain second data enabling logical data transfer for processing by the first processor and to facilitate first products of interest pertaining thereto; and
a third processor embedded as a scalable health management system residing on a third platform of the plurality of platforms, the third health management system comprising a plurality of sibling services configured to request information from the third processor for use in controlling system processing, establishing specific data needs for system operations, facilitating products of local systems and services, servicing data requests from within and outside of a third platform, the third processor linked with the first processor and the second processor and configured to:
obtain third data from the third health management system;
obtain the first data and the first products of interest through the discoverable communication network;
process the first data, the second data, and the third data, to thereby generate a health determination for the first platform, the second platform, and the third platform;
establish products of interest being produced by the sibling services;
establish products produced by systems and services in proximity thereto; and
provide data transfer from multiple sources and to multiple destinations,
wherein the second processor is further dynamically configured and established to obtain the third data and to facilitate first products of interest pertaining thereto.

2. The system of claim 1, further comprising:
a plurality of service systems residing on the second platform, each service system configured to provide a request for information from the second processor, wherein the second processor is configured to provide the information to the service system via the health determination in the first processor or the second processor as dynamically established.

3. The system of claim 1, further comprising:
a plurality of onboard sensors residing on the second platform and configured to provide sensor data to the second health management system for use in generating the second data.

4. The system of claim 1, wherein the third processor is further configured to determine deployment options for the sibling services and data needed by the sibling services.

5. The system of claim 1, wherein the first processor is further configured to:
obtain the second data along the communication network;
obtain the third data along the communication network; and
process the first data, the second data, and the third data, to thereby generate a first health determination for the first platform, a second health determination for the second platform, and a third health determination for the third platform.

6. The system of claim 5, further comprising:
a plurality of service systems residing on the first platform, each service system configured to provide a request for information from the first processor, wherein the first processor is configured to provide the information to the service system via the second health determination, wherein the second processor is further configured to determine deployment options for the plurality of service systems.

7. The system of claim 1, further comprising:
a third processor embedded within a third health management system residing on a third platform of the plurality of platforms, the third processor coupled to the first processor and the second processor and configured to:
obtain the first data along the communication network;
obtain the second data along the communication network;
obtain the third data along the communication network; and
process the first data, the second data, and the third data, to thereby generate three health determinations for the first platform, the second platform, and the third platform.

8. The system of claim 7, further comprising:
a plurality of service systems residing on the third platform, each service system configured to provide a request for information from the third processor, wherein the third processor is configured to provide the information to the service system via the third health determination.

9. A method for health monitoring of one or more of a plurality of platforms, the method comprising the steps of:
obtaining first data pertaining to operation of a first platform of the plurality of platforms from a first health management system residing on the first platform via a first processor;
obtaining second data pertaining to operation of a second platform of the plurality of platforms from a second health management system residing on the second platform via a second processor;
obtaining the first data and the second data along a communication network via a third processor;
processing the first data and the second data, to thereby generate health determinations for each of the first platform and the second platform via the third processor;
establishing products of interest being produced by each of a plurality of sibling services;
establishing products produced by systems and services in proximity thereto; and
providing data transfer from multiple sources and to multiple destinations.

10. The method of claim 9, further comprising the steps of:
obtaining a request for information from a service system residing on the second platform via the second processor; and
providing the information to the service system via the health determinations using the second processor.

11. The method of claim 9, further comprising the steps of:
obtaining sensor data from a plurality of onboard sensors; and
providing the sensor data to the second health management system for use in generating the second data.

12. The method of Claim 9, further comprising the steps of:
obtaining the second data along the communication network via the first processor; and
processing the first data and the second data, to thereby generate a second health determination for the first platform.

13. The method of claim 12, further comprising the steps of:
obtaining a request for information form a service system residing on the first platform via the first processor; and
providing the information to the service system via the second health determination using the first processor.

14. The method of claim 9, further comprising the steps of:
obtaining the first data along the communication network via a third processor residing on a third platform;
obtaining the second data along the communication network via the third processor; and
processing the first data and the second data, to thereby generate a third health determination for the first platform, the second platform, or both, via the third processor.

15. The method of claim 14, further comprising the step of:
generating a fourth health determination for the third platform using the first data and the second data, via the third processor.

16. The method of claim 14, further comprising the steps of:
obtaining a request for information form a service system residing on the third platform via the third processor; and
providing the information to the service system via the health determination using the third processor.

17. A system comprising:
a communication network;
a first processor embedded within a first health management system residing on a first platform of a plurality of platforms and configured to obtain first data pertaining to operation of the first platform from the first health management system and provide the first data on the communication network;
a second processor embedded within a second health management system residing on a second platform of the plurality of platforms, the second processor coupled to the first processor and configured to obtain second data pertaining to operation of the second platform and provide the second data on the communication network; and
a third processor residing on a third platform of the plurality of platforms, the third processor coupled to the first processor and to the second processor and configured to:
obtain the first data along the communication network;
obtain the second data along the communication network;
process the first data and the second data, to thereby generate health determinations for both of the first platform and the second platform;
establish products of interest being produced by each of a plurality of sibling services;
establish products produced by systems and services in proximity thereto; and
provide data transfer from multiple sources and to multiple destinations.

18. The system of claim 17, further comprising:
a plurality of service systems residing on the third platform, each service system configured to provide a request for information from the third processor, wherein the third processor is configured to provide the information to the service system via the second health determination.

* * * * *

UNITED STATES PATENT AND TRADEMARK OFFICE
CERTIFICATE OF CORRECTION

PATENT NO. : 8,090,824 B2
APPLICATION NO. : 12/645921
DATED : January 3, 2012
INVENTOR(S) : Tran et al.

Page 1 of 1

It is certified that error appears in the above-identified patent and that said Letters Patent is hereby corrected as shown below:

IN THE CLAIMS:
Column 19, line 20, claim 13, "form" should be changed to --from--;
Column 19, line 39, claim 16, "form" should be changed to --from--.

Signed and Sealed this
Fifth Day of June, 2012

David J. Kappos
*Director of the United States Patent and Trademark Office*